US00PP22214P2

(12) United States Plant Patent
Hartman

(10) Patent No.: US PP22,214 P2
(45) Date of Patent: Oct. 25, 2011

(54) ***CALADIUM* PLANT NAMED 'PEPPERMINT'**

(50) Latin Name: *Caladium×hortulanum*
Varietal Denomination: Peppermint

(76) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 12/800,181

(22) Filed: May 10, 2010

(51) Int. Cl.
*A01H 5/00* (2006.01)

(52) U.S. Cl. ..... Plt./373

(58) Field of Classification Search ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Peppermint', characterized by its upright and mounding plant habit; intermediate plant size; vigorous and dense growth habit; rapid growth rate; lance-type leaves that are red purple and white in color with dark green-colored margins and white-colored venation.

4 Drawing Sheets

Botanical designation: *Caladium×hortulanum.*
Cultivar denomination: 'PEPPERMINT'.

BACKGROUND OF THE INVENTION

The present invention relates to a new and distinct cultivar of *Caladium* plant, botanically known as *Caladium×hortulanum*, commercially referred to as a lance leaf-type *Caladium* and hereinafter referred to by the name 'Peppermint'.

The objective of the Inventor's breeding program is to create new *Caladium* plants that have uniform plant habit, exceptional container and garden performance and attractive foliage coloration.

The new *Caladium* plant originated from a cross-pollination made by the Inventor in April, 2002, in Lake Placid, Fla. of *Caladium×hortulanum* 'Pink Symphony', not patented, as the female, or seed, parent with *Caladium×hortulanum* 'White Wing', not patented, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2003.

Asexual reproduction of the new *Caladium* plant by tuber divisions in a controlled outdoor nursery environment in Lake Placid, Fla. since Apr. 15, 2004 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'Peppermint'. These characteristics in combination distinguish 'Peppermint' as a new and distinct *Caladium* plant:

1. Upright and mounding plant habit; intermediate plant size.
2. Vigorous and dense growth habit; rapid growth rate.

3. Lance-type leaves that are red purple and white in color with dark green-colored margins and white-colored venation.

Plants of the new *Caladium* differ primarily from plants of the female parent, 'Pink Symphony', in the following characteristics:

1. Leaves of plants of the new *Caladium* are broader than leaves of plants of 'Pink Symphony'.
2. Plants of the new *Caladium* and 'Pink Symphony' differ in leaf coloration as plants of 'Pink Symphony' have light pink-colored leaves with green-colored margins and venation.

Plants of the new *Caladium* differ primarily from plants of the male parent, 'White Wing', in the following characteristics:

1. Plants of the new *Caladium* had broader leaves than plants of 'White Wing'.
2. Plants of the new *Caladium* and 'White Wing' differ in leaf color as plants of 'White Wing' have white and green-colored leaves with green-colored mottled margins and pink to creamy white-colored venation.

Plants of the new *Caladium* can be compared to plants of 'Florida Sweetheart', disclosed in U.S. Plant Pat. No. 8,526. In side-by-side comparisons conducted in Lake Placid, Fla., plants of the new *Caladium* differed primarily from plants of 'Florida Sweetheart' in the following characteristics:

1. Plants of the new *Caladium* were larger than plants of 'Florida Sweetheart'.
2. Plants of the new *Caladium* had narrower leaves than plants of 'Florida Sweetheart'.
3. Plants of the new *Caladium* and 'Florida Sweetheart' differed in leaf coloration as plants of 'Florida Sweetheart' had dark pink-colored leaves with thin green-colored margins and rose red-colored venation.

Plants of the new *Caladium* can also be compared to plants of 'Thai Beauty', not patented. In side-by-side comparisons conducted in Lake Placid, Fla., plants of the new *Caladium* differed primarily from plants of 'Thai Beauty' in the following characteristics:

1. Plants of the new *Caladium* had broader leaves than plants of 'Thai Beauty'.

2. Plants of the new *Caladium* and 'Thai Beauty' differed in leaf coloration as plants of 'Thai Beauty' had pink-colored leaves with thin green-colored margins and white to greenish white-colored venation.

BRIEF DESCRIPTION OF THE PHOTOGRAPHS

The accompanying photographs illustrate the overall appearance of the new *Caladium* plant. These photographs show the colors as true as it is reasonably possible to obtain in colored reproductions of this type.

Colors in the photographs may differ slightly from the color values cited in the detailed botanical description which accurately describe the colors of the new *Caladium* plant.

The photograph on the first sheet is a side perspective view of a typical plant of 'Peppermint' grown in a container in a shadehouse.

The photograph on the second sheet is a close-up view of typical inflorescences of 'Peppermint'.

The photograph at the top of the third sheet is a top perspective view of typical plants of 'Peppermint' grown in an outdoor nursery.

The photograph at the bottom of the third sheet is a close-up view of typical freshly-dug tubers and roots of 'Peppermint'.

The photograph at the top of the fourth sheet is a side perspective view of typical potted plants of 'Peppermint' (center), 'White Wing' (left) and 'Pink Symphony' (right).

The photograph at the bottom of the fourth sheet is a side perspective view of typical potted plants of 'Peppermint' (center), 'Thai Beauty' (left) and 'Florida Sweetheart' (right).

DETAILED BOTANICAL DESCRIPTION

The aforementioned photographs and following observations and measurements describe plants grown during the spring and summer in 15-cm containers in Avon Park, Fla. in a polypropylene-covered shadehouse (30% shade) and plants grown during the spring and summer in ground beds in Zolfo Springs, Fla. during the late summer in an outdoor nursery. All plants were grown under conditions and practices which approximate those generally used in commercial *Caladium* production. During the production of the plants, day temperatures ranged from about 20° C. to 35° C., night temperatures ranged from about 10° C. to 26° C. and light levels were about 8,000 foot-candles (shadehouse) or 10,000 to 12,000 foot-candles (outdoor nursery). Plants had been growing in the shadehouse for eight weeks from planting tubers when the photographs and the detailed description were taken. Plants had been growing in the outdoor nursery for six months from planting tuber divisions when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Peppermint'.

Parentage:

*Female, or seed, parent.*—*Caladium×hortulanum* 'Pink Symphony', not patented.

*Male, or pollen, parent.*—*Caladium×hortulanum* 'White Wing', not patented.

Propagation:

*Type.*—By tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate in shape. Height: About 3.2 cm. Diameter: About 3 cm. Texture: Thick and starchy; somewhat brittle. Color: Epidermis, between 164D and 160D; with development, close to 200A to 200B; interior, close to 1D. Root description: Dense, thick, fleshy contractile roots with few lateral branches; color, close to 155C.

Plant description:

*Plant type.*—Herbaceous perennial; suitable as a potted plant in containers 15-cm to 25-cm and also suitable as a landscape plant.

*Plant and growth habit.*—Upright and mounding plant habit; intermediate plant size; inverted triangle; vigorous and dense growth habit; rapid growth rate; petioles and leaves arise from one or more growing points on tubers; petioles mostly upright and leaning outwardly with development.

*Plant height, from soil level to top of leaf plane, shadehouse-grown plants.*—About 29 cm to 33 cm.

*Plant height, from soil level to top of inflorescences, shadehouse-grown plants.*—About 33.5 cm.

*Plant diameter or spread, shadehouse-grown plants.*—About 47 cm to 53 cm.

*Number of clumps per plant, shadehouse-grown plants.*—About eleven from tubers.

*Cataphylls, shadehouse-grown plants.*—Length: About 7 cm. Width: About 1.7 cm. Shape: Lanceolate to narrowly elliptic. Apex: Acuminate. Base: Sheathing the stem. Color, inner and outer surfaces: Between 177D and N170D tinged with close to 147B, streaked with close to 147A and N186C; with development, color becoming closer to 200C.

Foliage description:

*Length, shadehouse-grown plants.*—About 19 cm to 22 cm.

*Width, shadehouse-grown plants* (*flattened*).—About 10.5 cm to 15.5 cm.

*Shape.*—Ovate.

*Apex.*—Acuminate.

*Base.*—Sagittate to peltate.

*Margin.*—Entire; undulate.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Ground color, close to 155C; random spots, streaks and sectors, close to 59A, 59B or 59C; basal notch, close to 59A. Margins: Between N189A and 147A; interior to dark green-colored margins are diffuse green-colored markings, close to 137A to 137B. Venation: Midrib, close to 196C to 196D tinged with close to 62D; distal midrib, between 155C and 192D; primary veins, close to 196C to 196D. Developing leaves, lower surface: Center: Ground color, close to 155C tinged with close to 145D and 139D; random spots, streaks and sectors, close to 59A, 59B or 59C; basal notch, close to 59A. Margins: Close to 147A and between 137A and 138A; interior to dark green-colored margins are diffuse green-colored markings, close to 139C and 137D. Venation: Midrib, between N170D and 148B to 148C; distal midrib, close to 147C; primary veins, close to 148B and 148C tinged with close to N170D. Fully expanded leaves, upper surface: Center: Ground color, close to 59B to 59C; random basal sectors, close to 155C tinged with close to 192D; basal notch, close to 59A. Margins: Between 147A and N189A.

Venation: Midrib, close to N155B to N155C streaked with close to 191A to 191B; distal midrib, close to 192C tinged and streaked with close to 191A to 191B; primary veins, close to N155B to N155C tinged and streaked with close to 191B. Fully expanded leaves, lower surface: Center: Ground color, close to 59B to 59C; random basal sectors, close to 155C tinged with close to 145D; basal notch, close to 59A. Margins: Between 137B and 191A. Venation: Midrib, close to N170D and 194B; distal midrib, between 191A and 137C; primary veins, between 194B and 147C.

*Color, field-grown plants.*—Developing leaves, upper surface: Center: Ground color, close to 155C, random spots, streaks and sectors, close to 59B or 59C; basal notch, close to 59A. Margins: Between 147A and 137A; interior to dark green-colored margins are diffuse green-colored markings, close to 137B to 137C. Venation: Close to 196C to 196D. Developing leaves, lower surface: Center: Ground color, more white than 155C; random spots, streaks and sectors, close to 59B; random sectors, close to 137B to 137C; basal notch, close to 59A. Margins: Close to 189A; interior to dark green-colored margins are diffuse green-colored markings, close to 146D. Venation: Midrib, between N170D and 194B; distal midrib, close to 194B; primary veins, between 194A and 147C; secondary veins, close to 146C to 146D tinged with close to 59D. Fully expanded leaves, upper surface: Center: Ground color, close to 155C; random spots, streaks and sectors, close to 59A or 59B; basal notch, close to 59A to 59B. Margins: Close to 147A or 147A tinged with close to N189A. Venation: Close to 196C often tinged with close to 59C to 59D. Fully expanded leaves, lower surface: Center: Ground color, close to 155C; random spots, streaks and sectors, close to 60A; random sectors, close to 137B to 137C; basal notch, close to 59A. Margins: Between 147A and 189A; interior to dark green-colored margins are diffuse green-colored markings, close to 137B to 137C. Venation: Midrib, close to N170D tinged with close to 194B; distal midrib, close to 194B; primary veins, close to 146D; secondary veins, close to 146D tinged with close to 59D.

*Petiole.*—Aspect: Mostly erect, outwardly arching with development; flexible. Length, shadehouse-grown plants: About 23 to 25 cm. Diameter, distal, shadehouse-grown plants: About 4 mm. Diameter, proximal, shadehouse-grown plants: About 1 cm. Color, proximal, shadehouse-grown plants: Close to 177D or N170D tinged with close to 147B; streaks tessellated with close to N186A and 147A. Color, distal, shadehouse-grown plants: Close to 147A to 147B. Wing length, shadehouse-grown plants: About 4.5 cm to 7 cm. Wing diameter, shadehouse-grown plants: About 1 cm. Wing color, shadehouse-grown plants, outer surface: Close to 159C tinged with close to N170D. Wing color, shadehouse-grown plants, inner surface: Close to N155C; streaks, close to N186B tinged with close to 147A.

Inflorescence description: Inflorescences observed on shadehouse-grown plants.

*Inflorescence arrangement.*—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop between female and male flower zones; near this area, the spathe constricts and surrounds and encloses the female flowers; spathe open and cupped around male flowers.

*Fragrance.*—None detected.

*Natural flowering season/longevity.*—Plants of the new *Caladium* typically flower during the spring or early summer in central Florida; flowers develop about eight weeks after growth commences; inflorescences last about three days before fading; inflorescences persistent.

*Spathe.*—Length: About 10 cm; open length, about 7 cm and closed length, about 3 cm. Width, distal: About 3.2 cm. Width, proximal: About 3 cm. Width, at constriction: About 1.8 cm. Shape: Ovate. Apex: Acuminate. Base: Tapering to the peduncle. Margin: Entire; reflexed. Texture, upper and lower surfaces: Smooth, glabrous. Color: Front surface: Upper two-thirds: Close to N155C to N155D tinged with close to 69B to 69C; margin variably marked with 186A and 186C to 186D; color becoming closer to 199C to 199D with development. Lower one-third: Close to 137B to 137C; towards the base, deeply tinged with close to 187A; color becoming closer to 137A to 137B variably mottled with close to 155A or 150D with development. Rear surface: Upper two-thirds: Close to between 69C to 69D and N155D; center flushed with close to N170D and streaked with close to 146C to 146D; margins, close to between 69C to 69D and N155D and variably marked with close to 186A and 186C to 186D. Lower one-third: Close to 137A to 137B variably mottled with close to 155A or 150D. Spadix: Length: About 9 cm. Length, male flower zone: About 7 cm. Length, female flower zone: About 2 cm. Diameter, male flower zone: About 9 mm. Diameter, sterile flower zone: About 7 mm. Diameter, female flower zone: About 1 cm. Shape: Columnar. Apex: Obtuse. Base: Obtuse. Aspect: Upright or curved. Color, mature, male zone: Between 11C and 158A. Color, mature, sterile zone: Between 11C and 158A. Color, mature, female zone: Between 161C and 16C to 16D. Male flowers: Quantity per spadix: About 297. Shape: Obovate. Height: About 2 mm. Diameter: About 2 mm. Anther color: Close to 158C. Amount of pollen: None observed. Female flowers: Quantity per spadix: About 260. Shape: Obovate. Height: About 3 mm. Diameter: About 2 mm. Stigma color: Between 161C and 16C to 16D. Ovary color: Close to 158D. Scape: Length: About 23.5 cm. Diameter: About 6 mm. Strength: Sturdy; flexible. Aspect: Erect or slightly curved. Texture: Smooth, glabrous; glaucous. Color: Close to 177D tinged with close to 147B and streaked/tessellated with close to N186A. Seed and fruit: Seed and fruit development have not been observed on plants of the new *Caladium*.

Disease/pest resistance: Plants of the new *Caladium* have been observed to be relatively tolerant to *Pythium* root rot and *Xanthomonas* leaf spot. Plants of the new *Caladium* have not been observed to be resistant to pests or other pathogens common to *Caladium* plants.

Temperature tolerance: Plants of the new *Caladium* have been observed to be tolerant to temperatures ranging from about 7° C. to about 40° C. and suitable for USDA Hardiness Zones 8A to 11.

It is claimed:

1. A new and distinct *Caladium* plant named 'Peppermint' as illustrated and described.

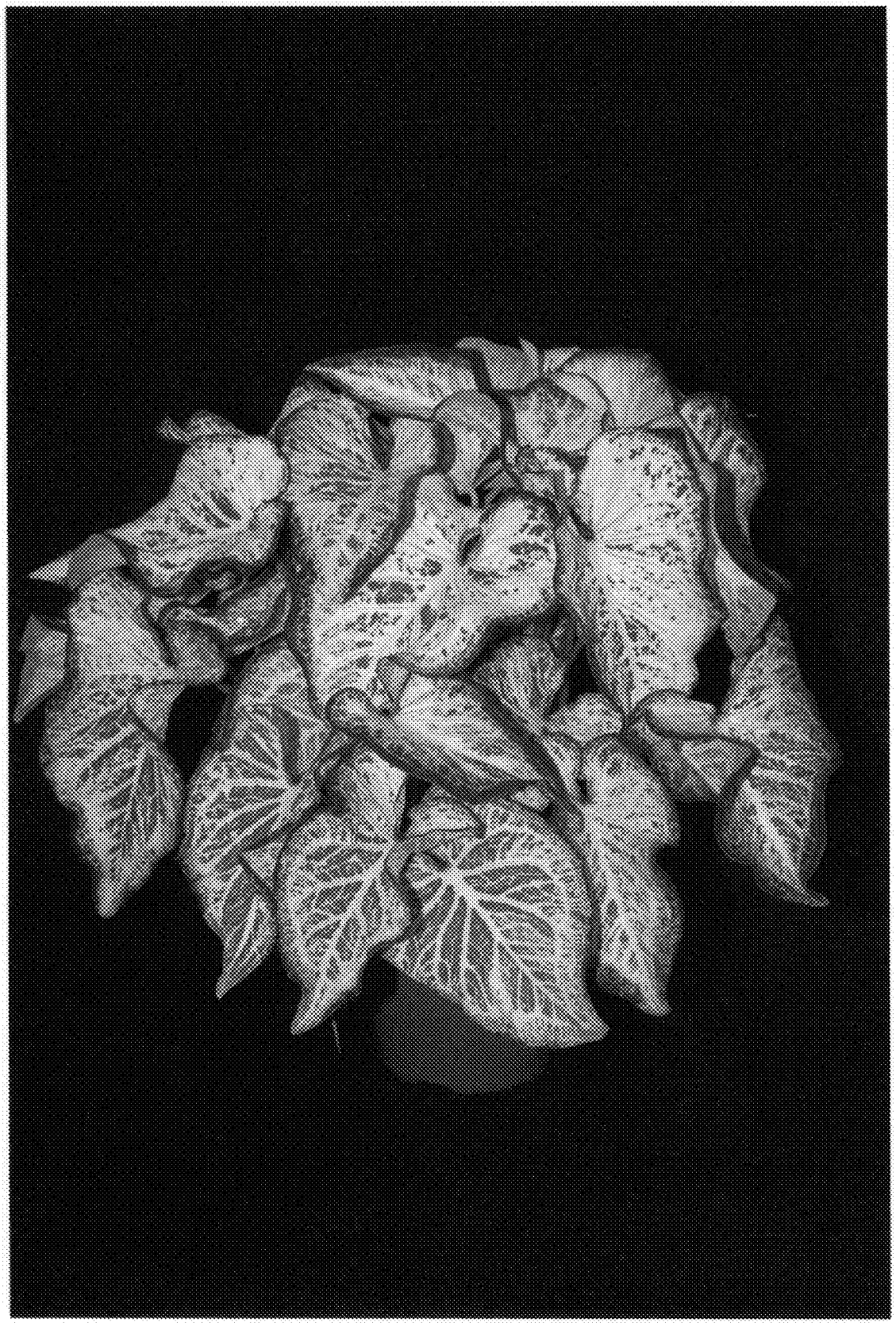

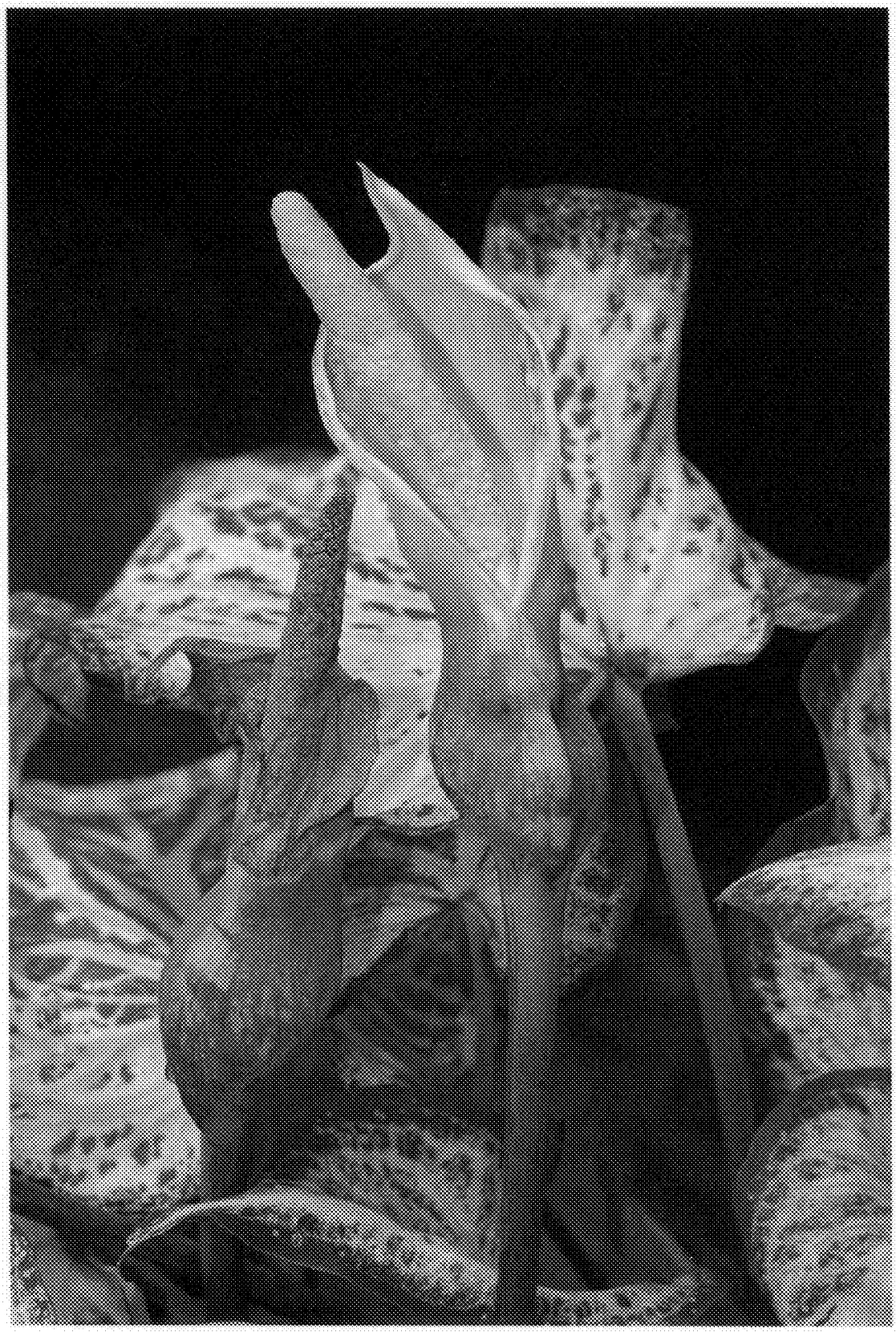

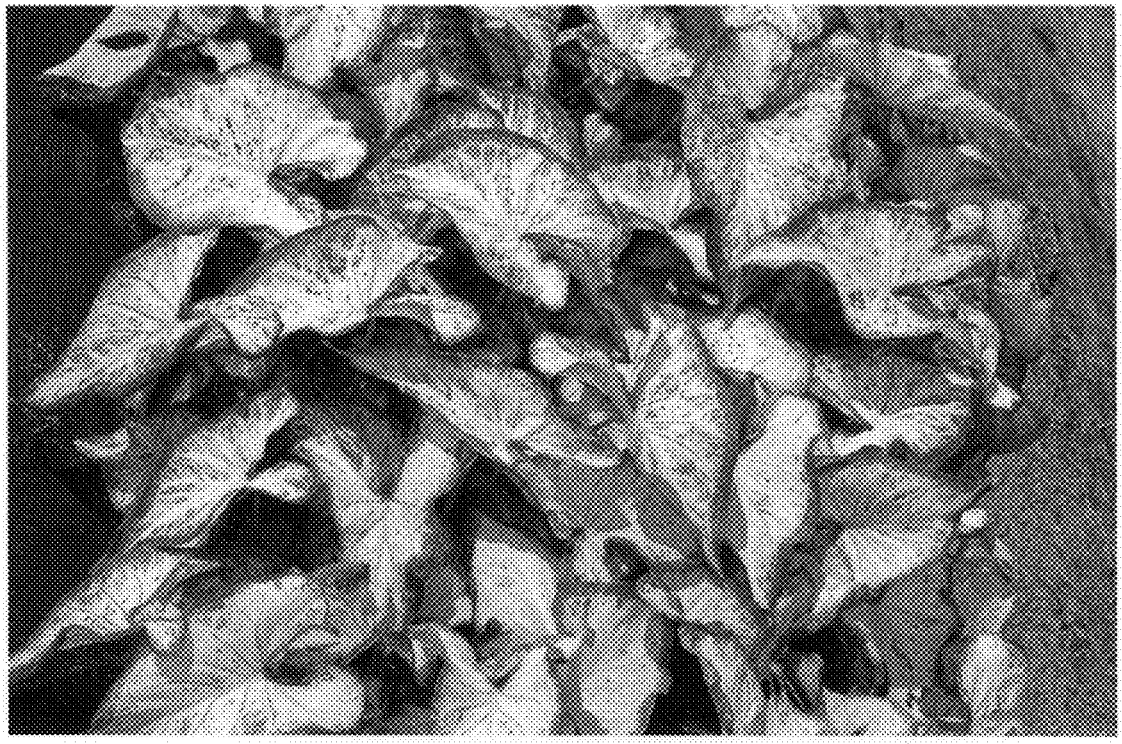
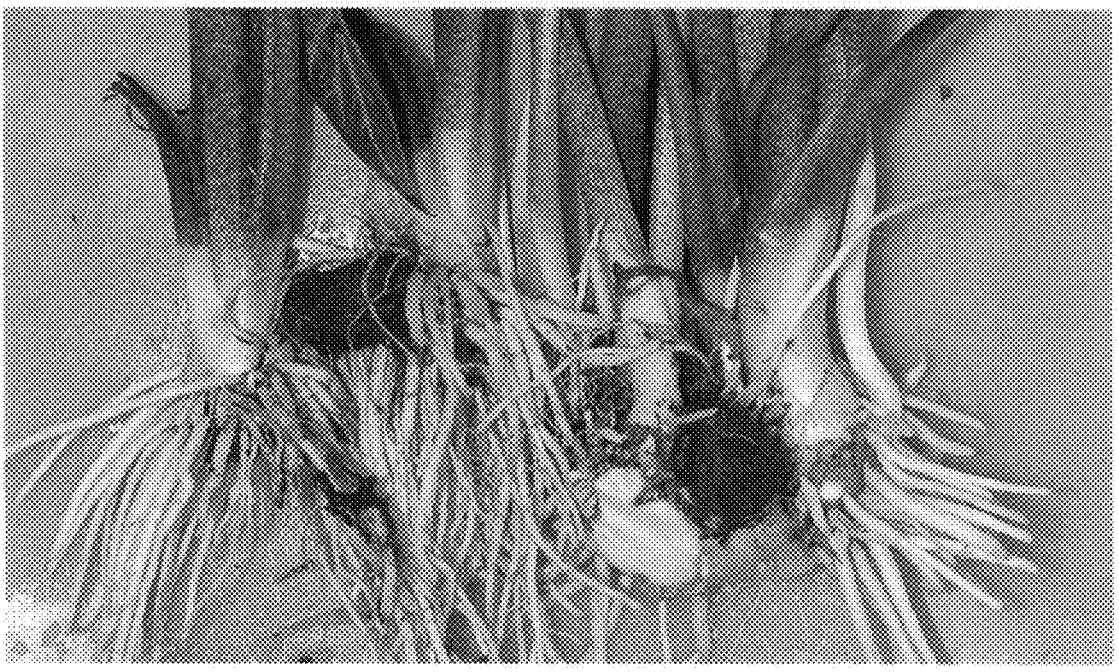

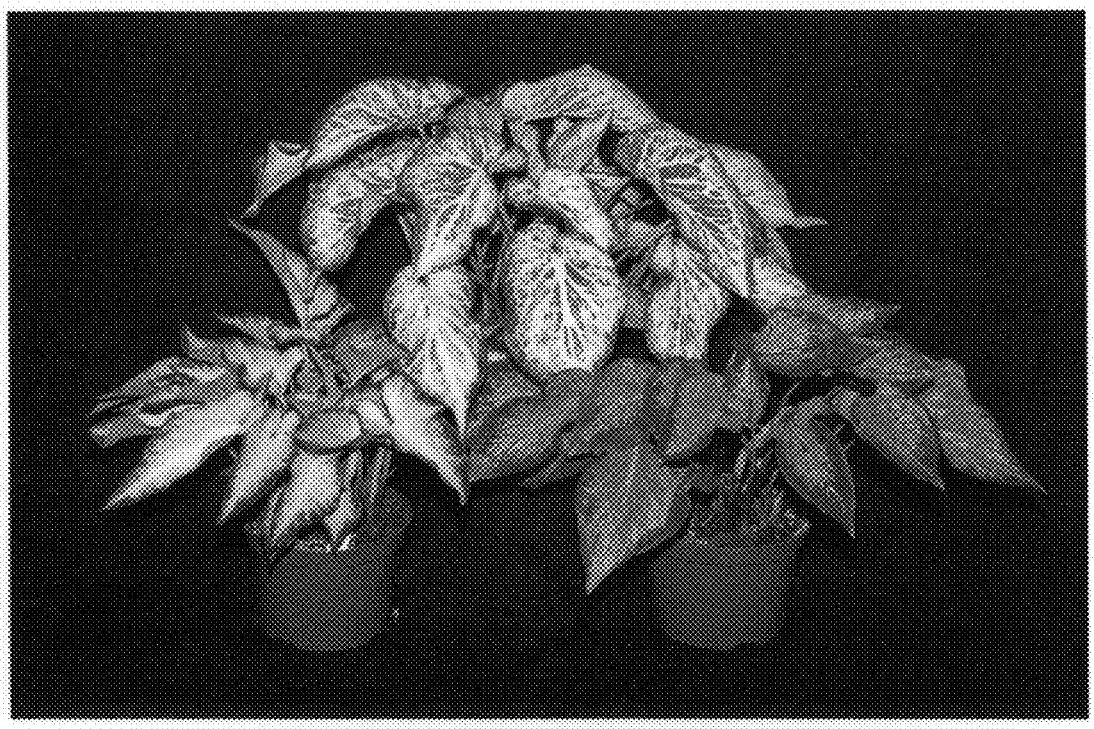
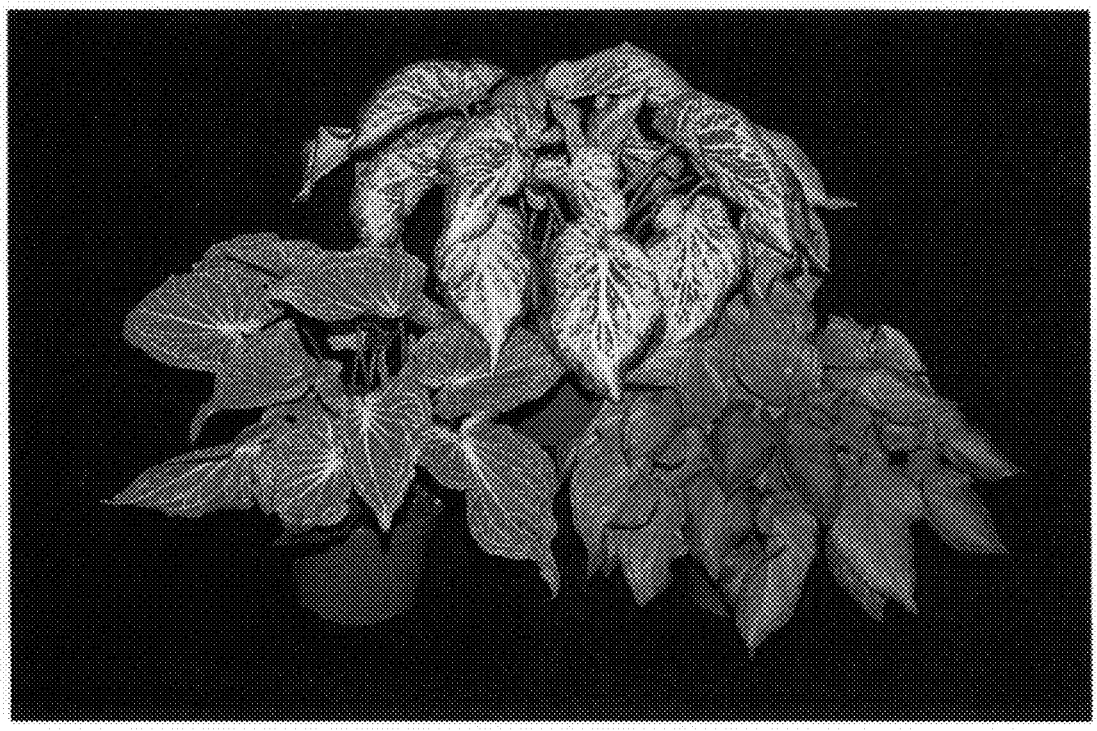

* * * * *